US010336988B2

(12) United States Patent
Buno et al.

(10) Patent No.: US 10,336,988 B2
(45) Date of Patent: Jul. 2, 2019

(54) METHODS FOR PURIFICATION OF A VIRUS PRODUCED IN VITRO AND CLEARANCE ASSAY FOR THE VIRUS

(71) Applicant: GRIFOLS, S.A., Barcelona (ES)

(72) Inventors: Brett Buno, Durham, NC (US); Terri Journigan, Wendell, NC (US); Joann Hotta, Raleigh, NC (US); Michael Burdick, Durham, NC (US)

(73) Assignee: GRIFOLS, S.A., Barcelona (ES)

( * ) Notice: Subject to any disclaimer, the term of this patent is extended or adjusted under 35 U.S.C. 154(b) by 68 days.

(21) Appl. No.: 15/213,740

(22) Filed: Jul. 19, 2016

(65) Prior Publication Data

US 2017/0022480 A1 Jan. 26, 2017

Related U.S. Application Data

(60) Provisional application No. 62/196,004, filed on Jul. 23, 2015.

(51) Int. Cl.

*C12N 7/00* (2006.01)
*C12Q 1/70* (2006.01)
*G01N 33/576* (2006.01)

(52) U.S. Cl.

CPC ............... *C12N 7/00* (2013.01); *C12Q 1/706* (2013.01); *C12Q 1/707* (2013.01); *G01N 33/576* (2013.01); *G01N 33/5768* (2013.01); *C12N 2770/28151* (2013.01)

(58) Field of Classification Search

None
See application file for complete search history.

(56) References Cited

U.S. PATENT DOCUMENTS 5,731,187 A 3/1998 Fanget et al.

OTHER PUBLICATIONS

Shukla et al. Journal of Virology vol. 86 No. 10, p. 5697-5707, year 2012.*
Takahashi et al. J Clin Microbiology vol. 48, pp. 1112-1125, year 2010.*
European Search Report, dated Dec. 7, 2016, received in Application No. 16179299.9.
Goerke, A. et al., Development of a novel adenovirus purification process utilizing selective precipitation of cellular DNA, Biotechnology and Bioengineering, vol. 91, No. 1, pp. 12-21, Jul. 5, 2005.
Okamoto, H., Hepatitis E virus cell culture models, Virus Research, vol. 161, No. 1, pp. 65-77, 2011.
Schielke, A. et al., Thermal Stability of hepatitis E virus assessed by a molecular biological approach, Virology Journal, vol. 8, No. 1, pp. 487, Oct. 31, 2011.
Takahashi, M. et al., Hepatitis E Virus (HEV) Strains in Serum Samples Can Replicate Efficiently in Cultured Cells Despite the Coexistence of HEV Antibodies: Characterization of HEV Virions in Blood Circulation, Journal of Clinical Microbiology, vol. 48, No. 4, pp. 1112-1125, Jan. 27, 2010.

* cited by examiner

*Primary Examiner* — Shanon A. Foley
*Assistant Examiner* — Myron G Hill
(74) *Attorney, Agent, or Firm* — Knobbe, Martens, Olson & Bear, LLP

(57) ABSTRACT

A method of purification of non-enveloped or pseudo-enveloped virus produced in vitro uses a composition with at least one detergent. A method of purification can use multiple detergents, and a method of determining the presence and/or level of a non-enveloped or pseudo-enveloped virus in a sample includes treating with at least one detergent.

22 Claims, 4 Drawing Sheets

Specification includes a Sequence Listing.

Lane 1 MW Markers

Lane 2 Cell Culture Media

Lane 3 Initial Crude HEV

Lane 4 TFF Retentate (dil 1:10 for gel)

Lane 5 Supernatant (dil 1:10 for gel)

Lane 6 TFF HEV

Lane 7 TFF Supe HEV (conc 5x for gel)

| Parameter | Initial Crude | TFF Retentate | Supernatant | TFF HEV | TFF Supe HEV |
|---|---|---|---|---|---|
| Volume (mL) | 500 | 50 | 50 | 1 | 1 |
| A280 | 4 | 41 | 41 | 3.8 | 0.8 |
| $Log_{10}$ HEV RNA copies/mL | 7.7 | 8.9 | 8.7 | 9.1 | 8.9 |

HEV-infected lysate
↓ Clarify/Filter thru 0.45um filter
Initial Crude HEV
↓ TFF (300kD membrane)
TFF Retentate
↓ Spin 85xg, 1.5h, 5C
Pellet
↓ Suspend in PBS
↓ Clarify/Filter thru 0.22um filter

Figure 4

5′-CGGCTATCGGCCAGAAGTT-3′ (SEQ ID NO: 1)

5′-CCGTGGCTATAACTGTGGTCT-3′ (SEQ ID NO: 2)

5′-FAM-TTTTTACGC-ZEN-AGGCTGCCAAGGCC-3IABkFQ-3′ (SEQ ID NO: 3)

METHODS FOR PURIFICATION OF A VIRUS PRODUCED IN VITRO AND CLEARANCE ASSAY FOR THE VIRUS

PRIORITY AND CROSS-REFERENCE TO RELATED APPLICATIONS

This application claims the benefit of priority to U.S. Provisional Application 62/196,004, filed on Jul. 23, 2015, which is hereby expressly incorporated by reference in its entirety.

REFERENCE TO SEQUENCE LISTING

The present application is being filed along with a Sequence Listing in electronic format. The Sequence Listing is provided as a file entitled DURC6_007AUS_SEQLIST.txt which is 1,081 bytes in size, created on Jul. 18, 2016 and last modified on Jul. 18, 2016. The information in the electronic format of the Sequence Listing is incorporated herein by reference in its entirety.

BACKGROUND

Field

The present invention refers to the field of virology, more precisely to methods of purification of non-enveloped or pseudo-enveloped virus such as hepatitis E virus (HEV), hepatitis A virus (HAV) and porcine parvovirus (PPV) propagated in cell culture and for use in virus clearance studies.

Description of the Related Art

Clinical use of all blood and plasma-derived products carries the potential risk of transmission of infectious blood-borne pathogens. Mitigation of risk can be achieved by the implementation of pathogen reduction steps in the manufacturing processes of blood and plasma-derived products. To develop and demonstrate the effectiveness of such pathogen reduction steps, virus clearance studies are performed. During these studies a known amount of virus is spiked into a blood or plasma product intermediate and then the spiked sample is processed using a bench scale model (a scaled down model) of the manufacturing process comprising a pathogen reduction step. Virus reduction and/or clearance during a pathogen reduction step is determined by comparing the amount of virus before and after the step.

To assure the validity of virus clearance data, the scaled down model must accurately represent a large scale unit operation and the virus spike should be representative of a potential contaminant. For example, cultivation of a virus spike in vitro may require serum, and the presence of serum in the virus spike could affect clearance studies that involve serum-free product intermediates. The presence of non-viral contaminants, such as extraneous host cell membranes, proteins and nucleic acids, could also interfere in the accurate assessment of virus clearance during a downstream step, where product intermediates are presumably highly purified. Therefore, it is important to remove virus spike contaminants that could impact the performance and relevancy of scaled down models.

SUMMARY

In some embodiments, the present invention comprises a method of purifying a non-enveloped or a pseudo enveloped virus propagated in cell culture, based on a method of treatment of a sample comprising the non-enveloped or the pseudo enveloped virus with a detergent. In some embodiments of the method, the virus propagated in cell culture is hepatitis A virus (HAV). In some embodiments of the method, the virus propagated in cell culture is porcine parvovirus (PPV). In some preferred embodiments of the method, the virus propagated in cell culture is hepatitis E virus (HEV). In some embodiments of the method, the virus is produced in an in vitro cell culture. In some embodiments of the method, the in vitro cell culture comprises an established cell line. In some embodiments of the method, the established cell line is selected from a group consisting of HepG2 (ATCC number HB-8065) and HepG2/C3A (ATCC number CRL-10741). In some embodiments of the method, the detergent is selected from the group consisting of Lithium Dodecyl Sulfate, Triton X-100 and mixtures thereof. In some embodiments of the method, a concentration of Triton X-100 is 0.5% and a concentration of Lithium Dodecyl Sulfate is 0.1%. In some embodiments of the method, the step of treating is carried out for 1 hour. In some embodiments of the method, the sample is a supernatant obtained from ultra-centrifugation of a clarified virus-infected cell lysate suspension. In some embodiments of the method, optionally, the sample is a retentate derived from transflow filtration of a clarified virus-infected cell lysate suspension.

A method of measuring a level of a non-enveloped or a pseudo-enveloped virus in a sample, the method comprising the steps of: a) providing the sample to a mixture comprising a cell line and a culture medium; b) incubating to allow propagation of the non-enveloped or the pseudo-enveloped virus, if present in the sample, to obtain an incubated portion; c) treating with at least one detergent, to obtain a treated portion; d) collecting a part of the treated portion, to obtain a collected portion; and e) measuring the level of the non-enveloped or the pseudo-enveloped virus in the collected portion. In some embodiments of the method, the sample is obtained from a mammal. In some embodiments of the method, the sample comprises plasma or blood. In some embodiments of the method, the non-enveloped or the pseudo-enveloped virus is HAV. In some embodiments of the method, the non-enveloped or the pseudo-enveloped virus is PPV. In some preferred embodiments of the method, the non-enveloped or the pseudo-enveloped virus is HEV. In some embodiments of the method, the virus is propagated in an in vitro cell culture comprising an established cell line. In some embodiments of the method, the cell line is selected from the group consisting of HepG2 (ATCC number HB-8065) and HepG2/C3A (ATCC number CRL-10741). In some embodiments of the method, the sample comprises a first retentate obtained by trans-flow filtering a part of the incubated portion through a membrane. In some embodiments of the method, optionally, the sample comprises a first supernatant obtained by trans-flow filtering a part of the incubated portion through a membrane to obtain a first retentate and centrifugating the first retentate. In some embodiments of the method, the sample is treated with at least one detergent or optionally a mixture of detergents to obtain a first solution, the method further comprises: a) providing a first pellet obtained by centrifugating the first solution; b) providing a second solution obtained by resuspending the first pellet in PBS (Phosphate Buffered Saline); c) providing a third solution obtained by clarifying the second solution; d) providing a first filtrate obtained by filtering the third solution using a membrane; and e) providing a second retentate obtained by ultrafiltering the first filtrate, wherein the second retentate comprises the treated portion. In some embodiments of the method, measuring the level of the non-enveloped or pseudo-enveloped virus comprises detecting a biological substance, wherein the biological substance comprises a polynucleotide sequence and/or a polypeptide sequence of a virus, and wherein the biological substance is an HEV ribonucleic acid. In some embodiments of the method, measuring the biological substance comprises: a) providing a first reaction mixture comprising the HEV ribonucleic acid obtained by mixing a part of the treated portion with a lysis solution; b) providing a second reaction mixture obtained by adding a first reagent to the first reaction mixture, wherein the second reaction mixture comprises a deoxyribonucleic acid that is complementary to the HEV ribonucleic acid; c) adding, to the second reaction mixture, a second reagent that is at least partially complementary to a sequence within the deoxyribonucleic acid; d) adding, to the second reaction mixture, a third reagent that is at least partially complementary to a sequence within the deoxyribonucleic acid; e) amplifying the sequence encompassed by the second and the third reagents within the deoxyribonucleic acid; and f) measuring a concentration of the amplified sequence. In some embodiments of the method, the second reagent and the third reagent comprises an oligonucleotide sequence selected from the group consisting of:

```
                                    (SEQ ID NO: 1)
 a) 5'-CGGCTATCGGCCAGAAGTT-3';

                                    (SEQ ID NO: 2)
 b) 5'-CCGTGGCTATAACTGTGGTCT-3'
and

                                    (SEQ ID NO: 3)
 c) 5'-FAM-TTTTTACGC-ZEN-AGGCTGCCAAGGCC-3IABkFQ-3'.
```

In some embodiments, the present invention comprises a method of purifying a non-enveloped or a pseudo enveloped virus propagated in cell culture, based on a method of treatment of a sample comprising the non-enveloped or the pseudo enveloped virus with a at least one anionic detergent, such as lithium dodecyl sulfate (LDS), or at least one non-ionic detergent, such as Triton X-100 or a combination of the two, allowing to obtain virus whose behaviour in clearance studies is presumably the same or nearly the same as those that could potentially be present in highly purified process streams. In some embodiments, the virus generated by some embodiments of the method described above would be an appropriate spike to test the virus reduction and/or clearance capacity of downstream steps in manufacturing processes for blood and/or plasma-derived proteins.

In some embodiments, the method of purifying a virus produced in cell culture, based on a method of treatment, comprises: clarification of a virus-infected material; trans-flow filtering at least part of the mixture through a membrane to obtain a first retentate; and centrifugating the first retentate to obtain a first supernatant. The method of treatment comprises: treating the first supernatant with at least one detergent to obtain a first solution; wherein the method further comprises: after said treating, centrifugating the first solution to obtain a first pellet; resuspending the first pellet to obtain a second solution; clarifying the second solution to obtain a third solution; filtering the third solution using a membrane to obtain a first filtrate; and ultrafiltering the first filtrate to obtain a second retentate which provides at least part of the treated portion to be collected; wherein said at least one detergent is selected from the group consisting of Lithium Dodecyl Sulfate, Triton X-100 and mixtures thereof; wherein a concentration of Triton X-100 is 0.5% and a concentration of LDS is 0.1%; wherein said treating the first supernatant with the at least one detergent is carried out for 1 hour.

In some embodiments, the method of purifying a virus produced in cell culture, based on a method of treatment, comprises: clarification of virus-infected material; trans-flow filtering at least part of the mixture through a membrane to obtain a first retentate. The method of treatment comprises: treating the first retentate with at least one detergent to obtain a first solution; wherein the method further comprises: after said treating, centrifugating the first solution to obtain a first pellet; resuspending the first pellet to obtain a second solution; clarifying the second solution to obtain a third solution; filtering the third solution using a membrane to obtain a first filtrate; and ultrafiltering the first filtrate to obtain a second retentate which provides at least part of the treated portion to be collected; wherein said at least one detergent is selected from the group consisting of Lithium Dodecyl Sulfate, Triton X-100 and mixtures thereof; wherein a concentration of Triton X-100 is 0.5% and a concentration of LDS is 0.1%; wherein said treating the first retentate with the at least one detergent is carried out for 1 hour.

BRIEF DESCRIPTION OF THE DRAWINGS

FIG. 4 shows the nucleotide sequences of primers and probes.

DETAILED DESCRIPTION

Figure 1:
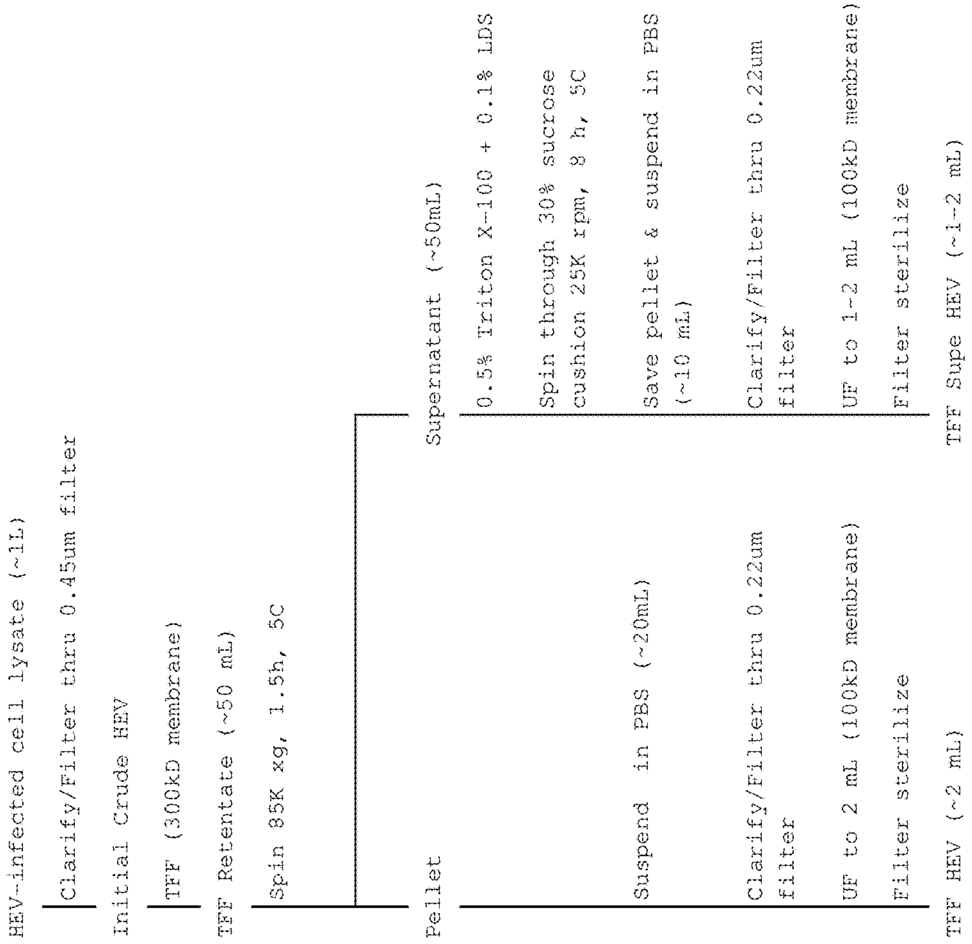
FIG. 1 shows preparation of Trans Flow Filtration HEV (TFF HEV) and TFF Supernatant (Supe) HEV virus spikes according to some embodiments disclosed herein.

Efficient cell culture systems for producing the non-enveloped virus HEV have recently been established and the data indicate that cell culture-derived HEV is similar to HEV found in blood in that they are both associated with lipids. As such, unprocessed clarified cell culture lysates or culture supernatants could be used as virus spikes in clearance studies of upstream steps with relatively crude product intermediates. However, the use of unprocessed virus spikes may not be appropriate for the evaluation of HEV clearance during downstream steps where process streams are of relatively high purity.

The invention relates to a process for preparing HEV spikes of relatively high purity and high titer that are suitable for use in virus clearance studies for downstream manufacturing process steps.

Because of the difficulties in culturing HEV in vitro, cell culture based HEV infectivity assays were not previously readily available. In some embodiments disclosed herein, propagation of high titer HEV in cell culture is possible by using media supplemented with polybrene.

Although HEV is technically considered a non-enveloped virus, HEV propagated in cell culture often comprises membrane fragments/lipids as it is released from cells. These membranous components may protect the virus from viricidal treatments, such as liquid heating or dry heating of lyophilized cakes. HEV can be treated with detergents such as Tween to remove membranous debris but the treated virus often remains resistant to inactivation by heating.

In some embodiments, the lipids associated with cell culture HEV can be removed by treatment with triton X-100. In some embodiments, the lipids associated with cell culture HEV can be removed by treatment with lithium dodecyl sulfate (LDS). In some embodiments, the lipids associated with cell culture HEV can be removed by treatment with a combination of triton X-100 and lithium dodecyl sulfate (LDS). In some embodiments, resulting virus preparation is still infectious. In some embodiments, the concentrations of the extraneous non-viral contaminants are reduced in the virus preparation. In some embodiments, the virus is also more susceptible to inactivation by viricidal treatments such as heating.

HEV does not produce cytopathic effects (CPE) in cell culture. Therefore, HEV detection is based on a PCR assay originally developed by the National Institutes of Health (NIH). In some embodiments, the PCR assay was modified to increase sensitivity. In some embodiments, one of the primers used in the PCR assay was altered. In some embodiments, the reverse primer used in the PCR assay was altered. In some embodiments, a probe used in the PCR assay was redesigned. A completely new probe was designed for the PCR assay. In some embodiments, the PCR assay was used to score samples as positive or negative for the determination of virus titers.

In some embodiments, the invention relates to a process that involves: propagation of high titer HEV in cell culture by using media supplemented with polybrene; treatment of cell culture HEV with triton X-100/LDS to remove membranous lipids/debris; and detection of HEV by a sensitive PCR assay.

In some embodiments, the process can be specific to HEV. In some embodiments, the methods for virus propagation and purification can be applied to other non-enveloped viruses. In some embodiments, the methods for virus propagation and purification can be applied to other pseudo-enveloped viruses. In some embodiments, the methods for virus propagation and purification can be applied to HAV. In some embodiments, the methods for virus propagation and purification can be applied to PPV. In some preferred embodiments, the methods for virus propagation and purification can be applied to HEV.

In some embodiments, the invention can be used to perform studies to evaluate HEV removal/inactivation capacity of various manufacturing steps and intermediate and final products. In some embodiments, the invention can be used to perform studies to evaluate removal/inactivation capacity of various manufacturing steps and intermediate and final products for other viruses. In some embodiments, the other viruses are non-enveloped viruses. In some embodiments, the other viruses are pseudo-enveloped viruses. In some embodiments, the other viruses are HAV and PPV.

In some embodiments, the invention can provide assurance on the safety of various medical or clinical products such as blood and/or plasma from HEV. In some embodiments, the invention can provide assurance on the safety of various medical or clinical products such as blood and/or plasma from other viruses. In some embodiments, the other viruses are HAV and PPV.

In some embodiments, the present invention relates to a method of purification of non-enveloped or pseudo-enveloped virus produced in vitro. In some embodiments, the present invention relates to a method of purification of HEV produced in vitro. In some embodiments, the purification comprises a detergent treatment step with a composition that comprises at least one anionic and/or one non-ionic detergent, such as lithium dodecyl sulfate and/or triton X-100.

In some embodiments, it is contemplated that in the composition comprising at least one detergent, the detergent is a non-ionic detergent. In some embodiments, it is contemplated that in the composition comprising a combination of detergents, one detergent is nonionic and the other is anionic. In some embodiments, it is contemplated that in the composition comprising at least one anionic detergent, the detergent is LDS. In some embodiments, it is contemplated that in the composition comprising at least one non-ionic detergent, the detergent is Triton X-100. In a preferred embodiment, the composition comprises more than one detergent. In a preferred embodiment, the composition comprises at least two detergents. In a preferred embodiment, the composition comprises one anionic detergent and one non-ionic detergent. In a preferred embodiment, the anionic detergent is LDS and the non-ionic detergent is Triton X-100.

In some embodiments, at least one detergent is used at a concentration adequate to exert its function in the method of purification of the present invention. In some embodiments, two detergents are used each at a concentration adequate to exert its function in the method of purification of the present invention. In some embodiments, the concentration of Triton X-100 in the range of 0.1% to 2.5% v/v. In some preferred embodiments, the concentration of Triton X-100 is 0.5% v/v. In some embodiments, the concentration of LDS is in the range of 0.02% to 0.5% v/v. In some preferred embodiments, the concentration of LDS is 0.1% v/v.

In some embodiments, the treatment with the composition comprising one or more detergents is carried out for a duration of time as required and determined by a person of ordinary skill in the art. In some embodiments, the treatment is carried out for 5 minutes to 1 day. In some preferred embodiments, the treatment is carried out for 10 minutes to 3 hour. In some preferred embodiments, the treatment is carried out for 1 hour.

In a most preferred embodiment, a composition comprising 0.5% of Triton X-100 and 0.1% of LDS is used and a step of treatment with the composition is carried out for 1 hour. In some embodiments, the incubation is carried out at 37° C. for 1 hour.

In some embodiments, as the starting material to carry out a method of purification of the present invention, a supernatant obtained from an ultracentrifugation of virus-infected cell culture medium or a clarified virus-infected cell lysate suspension, both derived from virally infected cell cultures, is used. In a preferred embodiment, the supernatant obtained from the ultracentrifugation of a clarified virus-infected cell lysate suspension is used.

In some embodiments, as the starting material to carry out a method of purification of the present invention, a retentate obtained after transflow filtration of virus-infected cell culture medium or a clarified virus-infected cell lysate suspension, both derived from virally infected cell cultures, is used. In a preferred embodiment, the retentate obtained after transflow filtration of a clarified virus-infect cell lysate suspension is used.

In a first embodiment, the purification method can comprise the following steps:

a) clarifying the starting material;

b) trans-flow filtering the solution of step a) through an appropriate membrane to obtain the corresponding retentate;

c) ultracentrifugation of the retentate of step b) to obtain the corresponding supernatant;

d) treating said supernatant of step c) with a detergent or a mixture of detergents to obtain the corresponding solution;

e) laying the solution of step d) onto a 30% sucrose cushion and carrying out ultracentrifugation at appropriate speed and time to obtain the corresponding pellet;

f) resuspending the pellet of step e) in the appropriate volume of PBS to obtain the corresponding solution;

g) clarifying the solution of step f) to obtain the corresponding solution;

h) ultrafiltering the solution obtained in step g) using an appropriate membrane to obtain the corresponding retentate; and i) filtering the retentate of step h).

In a preferred first embodiment, in step a), the starting material is clarified through a filter with 0.45 μm pore size.

In a preferred first embodiment, in step b), the membrane used to perform the trans-flow filtration is a 300 kDa membrane.

In a preferred first embodiment, in step c), ultracentrifugation is performed at 85,000×g for 1.5 hours.

In a preferred first embodiment, in step d), when a mixture of detergents is used, the mixture of detergents comprises 0.5% Triton X-100 and 0.1% LDS.

In a preferred first embodiment, in step e) ultracentrifugation is carried out at 100,000×g for 8 hours.

In a preferred first embodiment, it is contemplated that, in step f), the pellet is resuspended in PBS.

In a preferred first embodiment, in step g), the solution of step f) is clarified through a filter with 0.2 μm pore size.

In a preferred first embodiment, in step h), the membrane used in the ultrafiltration is a 100 kDa membrane.

In a preferred first embodiment, in step i), filtration is performed through a filter of 0.2 μm pore size.

In a second embodiment, a purification method can comprise the following steps:

a) clarifying the starting material;

b) trans-flow filtering the solution of step a) through an appropriate membrane to obtain the corresponding retentate;

c) treating said retentate of step b) with a detergent or a mixture of detergents to obtain the corresponding solution;

d) ultracentrifuging the detergent-treated solution at an appropriate speed and for an appropriate time to obtain the corresponding pellet;

e) resuspending the pellet of step d) in the appropriate volume of PBS to obtain the corresponding solution;

f) clarifying the solution of step e) to obtain the corresponding solution;

g) ultrafiltering the solution obtained in step f) is using the appropriate membrane to obtain the corresponding retentate; and h) filtering the retentate of step g).

In a preferred second embodiment, in step a), the starting material is clarified through a filter with 0.45 μm pore size.

In a preferred second embodiment, in step b), the membrane used to perform the trans-flow filtration is a 300 kDa membrane.

In a preferred second embodiment, in step c), when a mixture of detergents is used, said mixture of detergents is 0.5% Triton X-100 and 0.1% LDS.

In a preferred second embodiment, in step d), ultracentrifugation is performed at 85,000×g for 1.5 hours.

In a preferred second embodiment, in step e), the pellet is resuspended in PBS.

In a preferred second embodiment, in step f), the solution of step e) is clarified through a filter with 0.2 μm pore size.

In a preferred second embodiment, in step g), the membrane used in the ultrafiltration is a 100 kDa membrane.

In a preferred second embodiment, in step h), filtration is performed through a filter of 0.2 μm pore size.

The present invention relates to the use of LDS and/or Triton X-100 in a method for the purification of a non-enveloped or a pseudo-enveloped virus produced in vitro. In some embodiments, the virus is non-enveloped. In some embodiments, the virus is pseudo-enveloped.

In a preferred embodiment, the virus produced in vitro is HEV. In some embodiments, the virus produced in vitro can be a virus other than HEV. In some embodiments, the virus produced in vitro is HAV. In some embodiments, the virus produced in vitro is PPV. In the most preferred embodiment, the virus produced in vitro is HEV.

In some embodiments, the production in vitro described above is carried out in an in vitro culture. In some embodiments, the in vitro culture is an in vitro organ, tissue or cell culture. In a preferred embodiment, the production in vitro is carried out in an in vitro cell culture.

In some embodiments, primary cell culture is used. In some embodiments, a cell culture line is used. Primary cells and cell culture lines can be derived from any organism. For example, in some embodiments, the use of insect cells is contemplated. In some embodiments, the use of mammalian cells is contemplated. In a preferred embodiment, a human cell culture line is used.

In a preferred embodiment, a liver cell line is used for HEV production and purification. In another preferred embodiment, a kidney cell line is used for HEV production and purification. In some embodiments, the liver cell line can be derived from a healthy or diseased liver. In some embodiments, the liver cell line can be a malignant or benign cell line. In some embodiments, the kidney cell line can be derived from a healthy or diseased kidney. In some embodiments, the kidney cell line can be a malignant or benign cell line. In a preferred embodiment, an established cell line is used. In some embodiments, the cell is HepG2 (ATCC number HB-8065). In some embodiments, the cell is HepG2/C3A (ATCC number CRL-10741).

In some embodiments, an HEV infectivity assay is used. In some embodiments, virus spikes with ~8 $\log_{10}$ infectivity titers can be prepared. The assay is of a relatively short duration (3-7 day assay). Little or no PCR background was observed and over 4 $\log_{10}$ reduction can be demonstrated. Thus, in some embodiments, a PCR-based virus detection assay is used. In some embodiments, a PCR-based HEV detection assay is used.

Additional Preferred Embodiments—1

In some embodiments, a method of preparing a non-enveloped or a pseudo-enveloped virus propagated in cell culture, the method comprising: a step of treating a sample comprising the non-enveloped or the pseudo-enveloped virus with a composition comprising of one or more detergents. In some embodiments of the method, the virus propagated in cell culture is HAV. In some embodiments of the method, the virus propagated in cell culture is PPV. In some preferred embodiments of the method, the virus propagated in cell culture is HEV. In some embodiments of the method, the virus is produced in an in vitro cell culture. In some embodiments of the method, the in vitro cell culture comprises an established cell line. In some embodiments of the method, the established cell line is selected from a group consisting of HepG2 (ATCC number HB-8065) and HepG2/C3A (ATCC number CRL-10741). In some embodiments of the method, detergent treatment is with Lithium Dodecyl Sulfate and/or Triton X-100. In some embodiments of the method, a concentration of Triton X-100 is 0.5% and a concentration of LDS is 0.1%. In some embodiments of the method, the step of treating is carried out for 1 hour. In some embodiments of the method, the sample is a supernatant obtained from ultra-centrifugation of a clarified virus-infected cell lysate suspension. In some embodiments of the method, the sample optionally is a retentate derived from transflow filtration of a clarified virus-infected cell lysate suspension.

Additional Preferred Embodiments—2

In some embodiments, a method of measuring a level of a non-enveloped or a pseudo-enveloped virus in a sample, the method comprising the steps of:

a) providing the sample to a mixture comprising a cell and a culture medium;
b) incubating to allow propagation of the non-enveloped or the pseudo-enveloped virus, if present in the sample, to obtain an incubated portion;
c) treating with at least a first detergent, to obtain a treated portion;
d) collecting a part of the treated portion, to obtain a collected portion; and
e) measuring the level of the non-enveloped or pseudo-enveloped virus in the collected portion.

In some embodiments of the method, the sample is obtained from a mammal. In some embodiments of the method, the sample comprises plasma or blood. In some embodiments of the method, the non-enveloped or pseudo-enveloped virus is HAV. In some embodiments of the method, the non-enveloped or pseudo-enveloped virus is PPV. In some preferred embodiments of the method, the non-enveloped or pseudo-enveloped virus is HEV. In some embodiments of the method, the virus is produced in a cell culture. In some embodiments of the method, the cell is selected from the group consisting of HepG2 (ATCC number HB-8065) and HepG2/C3A (ATCC number CRL-10741). In some embodiments of the method, the sample comprises a first retentate obtained by trans-flow filtering a part of the incubated portion through a membrane. In some embodiments of the method, the sample optionally comprises a first supernatant obtained by trans-flow filtering a part of the incubated portion through a membrane to obtain a first retentate and centrifugating the first retentate. In some embodiments of the method, the sample is treated with at least the first detergent or optionally a mixture of detergents to obtain a first solution. In some embodiments, the method further comprises:

a) providing a first pellet obtained by centrifugating the first solution;
b) providing a second solution obtained by resuspending the first pellet in PBS;
c) providing a third solution obtained by clarifying the second solution;
d) providing a first filtrate obtained by filtering the third solution using a membrane; and
e) providing a second retentate obtained by ultrafiltering the first filtrate, wherein the second retentate comprises the treated portion.

In some embodiments of the method, measuring the level of the non-enveloped or pseudo-enveloped virus comprises detecting a biological substance. In some embodiments of the method, the biological substance comprises a polynucleotide sequence and/or a polypeptide sequence of a virus. In some embodiments of the method, the biological substance is an HEV ribonucleic acid. In some embodiments of the method, measuring the biological substance comprises:

a) providing a first reaction mixture comprising the viral ribonucleic acid obtained by mixing a part of the treated portion with a lysis solution;
b) providing a second reaction mixture obtained by adding a first reagent to the first reaction mixture, wherein the second reaction mixture comprises a deoxyribonucleic acid that is complementary to the viral RNA;
c) adding, to the second reaction mixture, a second reagent that is complementary to a sequence within the deoxyribonucleic acid;
d) adding, to the second reaction mixture, a third reagent that is complementary to a sequence within the deoxyribonucleic acid;
e) amplifying the sequence encompassed by the second and the third reagents within the deoxyribonucleic acid; and
f) measuring a concentration of the amplified sequence.

In some embodiments of the method, the second reagent and the third reagent comprises an oligonucleotide sequence selected from the group consisting of:

a) 5'-CGGCTATCGGCCAGAAGTT-3' (SEQ ID NO: 1);
b) 5'-CCGTGGCTATAACTGTGGTCT-3' (SEQ ID NO: 2) and
c) 5'-FAM-TTTTTACGC-ZEN-AGGCTGCCAAGGCC-3IABkFQ-3' (SEQ ID NO: 3).

Additional Preferred Embodiments—3

In some embodiments, for clarification of virus, a frozen crude virus stock is used. In some embodiments, when preparing a concentrated and purified non-enveloped virus stock 0.5% Triton X-100 and 0.1% LDS are added to a thawed crude virus stock and incubated at 37° C. for 1 hour.

In some embodiments, clarification of the thawed crude virus stock is performed by centrifugation at a speed of 3000 to 8000×g for 15 to 30 minutes at 2° C. to 8° C. In some embodiments, the supernatant is removed and retained and the pellet discarded. In some embodiments, the supernatant is filtered through a 0.45 μm filter, before transflow filtration through a 300 k Da membrane and a TFF retentate is collected.

In some embodiments, for ultracentrifugation, the TFF retentate is ultracentrifuged in ultracentrifuge tubes in a swinging bucket rotor at 2° C. to 8° C. for 1.5 hours at approximately 85000×g. In some embodiments, the supernatant from the ultracentrifugation is decanted and discarded as liquid waste.

In some embodiments, for ultrafiltration, the ultracentrifugation pellet is resuspended in no less than 5 mL buffer, such as PBS. In some embodiments, the pellet suspension is clarified at 3000 to 4200×g for 15 minutes at 2° C. to 8° C. In some embodiments, the supernatant is removed and placed into an Amicon® UF filter device to concentrate. In some embodiments, if required, buffer such as PBS is added to bring the final volume to approximately 15 mL (filter capacity is 15 mL).

In some embodiments, the filter device is centrifuged at approximately 5000×g at 2° C. to 8° C. until the retained sample (concentrated and purified virus stock) final volume is no more than 1 mL. In some embodiments, the approximate centrifuge time is about 15 to about 60 minutes.

In some embodiments, the concentrated and purified virus stock is aliquoted and frozen at no more than −65° C.

EXAMPLES

Example 1. Preparation of TFF-HEV Spikes

Tangential flow filtration (TFF) is a well-known procedure for separation and concentration of biomolecules. Additional information concerning TFF is readily available, for example in "Introduction to Tangential Flow Filtration for Laboratory and Process Development Applications" by Larry Schwartz et al. (pall.com/main/laboratory/literature-library-details.page?id=34212), which is incorporated by reference herein in its entirety.

HEV-infected HepG2 or HepG2/C3A cells were frozen and thawed two times and clarified by low speed centrifugation and passage through a 0.45 μm filter. The clarified solution (~1 L) was concentrated ten-fold by TFF through two 300 kDa membranes and the resulting TFF retentate (~100 mL) was spun at approximately 85,000×g, 90 minutes, 4° C. to pellet the virus. The ultracentrifuge supernatant (~100 mL) was collected and saved for processing to TFF-Supe HEV (Example 2) while the pellet was resuspended in PBS. The resuspended pellet was then filtered through a 0.2 μm pore filter and ultrafiltered through a 100 kDa membrane to a final volume of approximately 2 mL. The solution was filter sterilized through either a 0.2 μm or a 0.1 μm filter and stored at 5° C. until ready for use as a TFF-HEV spike preparation.

Example 2. Preparation of TFF-Supernatant HEV (TFF-Supe HEV) Spikes

Lipids associated with cell culture-derived HEV increase virus buoyancy and, thereby, decrease the efficiency of virus pelleting by ultracentrifugation. Thus, in some embodiments of the present invention, a detergent mixture comprising Triton X-100 and lithium dodecyl sulfate (LDS) is added to HEV-containing fluids to remove the associated lipids and to increase virus recoveries.

Approximately 100 mL of the ultracentrifuge supernatant, that resulted from TFF and ultracentrifugation of clarified HEV-infected cell lysates (~1 L) of Example 1, was treated with 0.5% Triton X-100 and 0.1% LDS for no less than 30 minutes, 37° C., before ultracentrifugation through a 30% sucrose cushion at 100,000×g, for 8 hours, 5° C. The resulting pellet was resuspended in PBS, filtered through a 0.2 μm pore filter and ultrafiltered through a 100 kDa membrane to a final volume of approximately 1 mL. The solution was then passed through either a 0.2 μm or a 0.1 μm filter and stored at 5° C. until ready for use as a TFF-Supe HEV spike preparation.

Example 3. Comparing the Purity of Viral Spikes Generated According to the Methods of Examples 1 and 2

Figure 2:
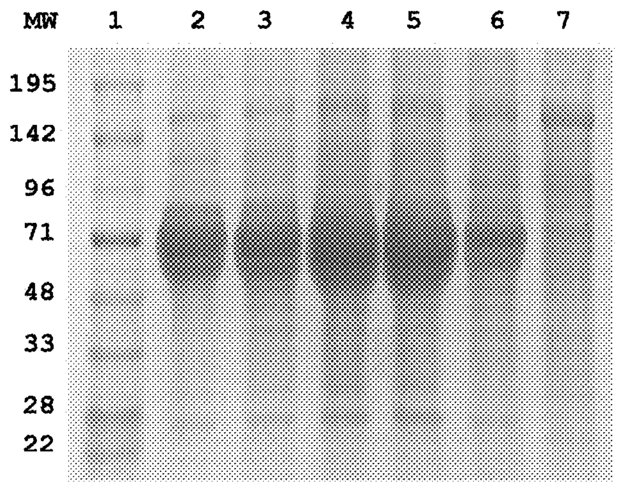
FIG. 2 shows the relative purity of TFF HEV and TFF Supe HEV virus spikes that were prepared according to some embodiments disclosed herein.

SDS-PAGE was used to compare the relative purity of the virus spikes generated according to the methods of Examples 1 and 2. As shown in FIG. 2, aliquots of the following samples were removed for A280 and quantitative PCR: Initial Crude HEV, TFF Retentate, Ultracentrifuge Supernatant, TFF-HEV and TFF-Supe HEV. TFF Retentate and Ultracentrifuge Supernatant had 10-fold more protein, as measured by A280, than Initial Crude HEV and TFF-HEV, and 40-fold more than TFF-Supe HEV (FIG. 2). Even though the protein concentrations were different, the concentrations of HEV RNA in all samples except the Initial Crude were approximately 9 $\log_{10}$ copies/mL (FIG. 2). Thus, the relative purity, as indicated by the ratio of virus (HEV RNA) to protein (A280) was much higher in TFF-Supe HEV and TFF-HEV than in Ultracentrifuge Supernatant and TFF Retentate.

The relative purity of samples could be visualized by SDS-PAGE (FIG. 2). Samples were diluted or concentrated to approximately 4 AU before heating in sample buffer containing DTT and loading onto 4-20% gradient gels. Cell culture media was also loaded as a background control. After SDS-PAGE, the gels were removed and stained with Instant Blue. The results were consistent with the A280 and PCR data in showing the highest impurity levels in TFF Retentate and Ultracentrifuge Supernatant. The most abundant protein banded at approximately 70 kDa. Since it was also present in the cell culture media, it was most likely a protein found in fetal bovine serum, a media supplement necessary for cell and virus propagation and a non-viral contaminant that could interfere in downstream clearance studies. Most of the contaminant was removed during the purification method described in Examples 1 and 2 and its relative concentrations were lowest in TFF Supe HEV, followed by TFF HEV.

Example 4. Comparing the Thermal Stability of Viral Spikes Generated According to the Methods of Examples 1 and 2

Experiments were conducted to compare the thermal stability of TFF-HEV and TFF-Supe HEV spikes that had been prepared according to Examples 1 or 2. Both virus preparations were spiked into PBS and incubated for 4 hours at 5° C., 60° C., 70° C. or 80° C. Aliquots were removed from each test solution and titrated as follows. Serial dilutions of a sample were made and added to wells seeded with HepG2 or HepG2/C3A cells. Virus was allowed to adsorb for no less than 1 hr at 37° C. and Growth Media was added. Plates were incubated at 37° C. for no less than 2 days before aspirating the media from the wells and washing/aspirating the cells no less than 2× with buffer (e.g. PBS). The plates were then extracted for viral RNA, using the Dynabeads® mRNA DIRECT™ Micro Kit (Life Technologies), or were stored at no warmer than −65° C. until ready for extraction. After extraction, the eluates (poly A RNA) was immediately processed for PCR amplification or stored at no warmer than −65° C. until ready for PCR amplification.

One step RT-PCR was used to detect HEV RNA in samples, using the following primers and probes as previously described. The assay conditions for each reaction were as follows:

a) Reagents; 5.0 μl 4× TaqMan® Fast Virus 1-Step Master Mix (Life Technologies), 0.08 μL 100 mM primer F+R, 0.04 μL 100 mM probe, 0.4 μL SUPERase In (Life Technologies), 4.4 μL water and 10 μL template (total 20 μl)

b) Reaction: 52° C. for 10 minutes, 95° C. for 30 seconds, and 40 cycles of 95° C. for 15 seconds, 56° C. for 45 seconds PCR and cycle threshold (Ct) value determinations were performed using an AB 7500 Real Time PCR System (Applied Biosystems, Foster City, Calif.) and accompanying software according to manufacturer's instruction. Based on historical data, the threshold was manually set at 0.1 so it passed through the exponential phase of all standard curves and to ensure detection of 1 RNA copy per reaction. A positive PCR signal, indicating the presence of HEV RNA, was registered any time the threshold was crossed.

All wells in a HEV titration plate were scored positive or negative based on the presence or absence of a positive PCR signal. Virus titers were then calculated as $TCID_{50}$/mL using the appropriate statistical methods: Spearman-Kärber, MPN or Poisson.

TABLE 1

Results obtained from experiments comparing the thermal stability of virus spikes in PBS

| Virus | $Log_{10}$ HEV Titer | | | | $Log_{10}$ Reduction Value | | |
|---|---|---|---|---|---|---|---|
| Spike | 5° C. | 60° C. | 70° C. | 80° C. | 60° C. | 70° C. | 80° C. |
| TFF HEV | 3.8 | NT | 1.8 | 1.7 | NA | 2.0 | 2.1 |
| TFF Supe HEV | 4.8 | ≤0.8 | ≤0.8 | ≤0.8 | ≥4.0 | ≥4.0 | ≥4.0 |

* Log Reduction Value (LRV) was calculated by subtracting the $\log_{10}$ HEV titer at 60° C., 70° C. or 80° C. from the $\log_{10}$ HEV titer at 5° C.
NT Not Tested
NA Not Applicable As shown in Table 1, virus inactivation was to the limit of detection at 60° C., 70° C. and 80° C. when viral spikes were prepared according to an embodiment of the method of the present invention (Example 2). On the other hand, when spikes obtained according to Example 1 (method of state of the art, no detergent treatment) were used, virus was still present after heating for 4 hours at 70° C. or 80° C.

Data from published reports suggest that the thermal stability of virus spikes generated according to Example 1 differs from the behaviour of HEV found in nature. For example, human enteric viruses are some of the most heat resistant viruses known and studies have shown 90% inactivation of hepatitis A virus, poliovirus and feline calicivirus, spiked into PBS, after heating at 72° C. for 18.35, 5.44, and 7.39 seconds (Suphachai N, Cliver D O. 2002. J Virol Methods 104: 217-225). In addition 1 hour, 60° C. heating of a liver suspension containing wild boar HEV, which is closely related to human HEV, resulted in 4.42 $\log_{10}$ virus reduction (Schielke A, et al. 2011. Virol Jol 8: 487-495). Thus, HEV spikes generated according to the method Example 1 (method of the state of the art, no detergent treatment) may not accurately assess the reduction of clinical isolates of HEV in virus clearance studies.

On the other hand, virus spikes generated according to the method of the present invention (Example 2) were completely inactivated by heat treatment, similar to that seen in HEV found in nature. As such, virus prepared according to the method of the present invention may be a more appropriate spike to use in virus clearance studies. Thus, in some embodiments, a virus spike is prepared according to the method of Example 2.

Example 5. Application of HEV Preparation Methods and Assay in Dry Heat Experiments As proof of principle, TFF-HEV and TFF-Supe HEV spikes were prepared as described in Examples 1 and 2 and tested in experiments to evaluate virus reduction and/or clearance during the freeze dry/dry heat (FD/DH) step of a Factor VIII concentrate manufacturing process. The FD/DH step is the last step of the manufacturing process and downstream a solvent/detergent (S/D) treatment step.

For the FD/DH experiments, Factor VIII concentrate spiked with either TFF-HEV or TFF-Supe HEV preparation was aliquoted into vials and freeze dried in a bench scale lyophilizer using the same freeze dry cycle as at manufacturing scale. The freeze dried vials were then placed in an 80° C. oven and dry heated for up to 75 hours.

Vials of virus-spiked product for titration were removed before (Initial) and after freeze drying and no dry heating (FD/DH 0 HR), after freeze drying followed by dry heating for 24 hours (FD/DH 24 h), and after free drying followed by dry heating 75 hours (FD/DH 75 hours). Virus-spiked FD/DH product was reconstituted with high purity water to its original volume, serially diluted, and inoculated onto HepG2 or HepG2/C3A cells that were seeded in a 96-well plate. Virus was adsorbed, final overlay media was added and the plates were placed in a 37° C. incubator for no less than 3 days. The titration plates were then removed, aspirated and extracted for viral RNA or stored at −80° C. until ready for extraction. Extracted RNA from each well was analysed for HEV by PCR as described in Example 3. Titration wells were scored positive or negative for HEV, and virus titers were determined. $Log_{10}$ HEV reduction during the step was calculated by comparing $\log_{10}$ virus titers in the initial and final (FD/DH 75 hours) vials.

TABLE 2

Results obtained from experiments comparing TFF-HEV and TFF-Supe HEV reduction by dry heat treatment

| | $Log_{10}$ HEV Titer | | | | |
|---|---|---|---|---|---|
| Virus Spike | Initial | FD/DH 0 h | FD/DH 24 h | FD/DH 75 h | LRV |
| TFF-HEV | 5.6 | 4.8 | 2.9 | 2.2 | 3.4 |
| TFF-Supe HEV | 5.2 | 4.7 | 1.4 | 0.6 | 4.6 |

* Log Reduction Value (LRV) was calculated by subtracting the 75 hr FD/DH treatment $\log_{10}$ HEV titer from the Initial $\log_{10}$ HEV titer.

As shown in Table 2, titers of both spike preparations were similar before and after freeze drying and reduction by freeze drying was not significant (less than 1 $\log_{10}$). In contrast, virus inactivation by 80° C. dry heat treatment was significant (greater than 1 $\log_{10}$) and greater for TFF-Supe HEV (LRV=4.6) than TFF HEV (LRV=3.4). The likely presence of high levels of contaminants in the TFF-HEV spike prepared according to the method of Example 1 may have protected the virus from inactivation by heat or may have impeded efficient destruction of encapsidated HEV RNA.

Since the starting material for the last step of FD/DH treatment is S/D treated in the penultimate step, any potential virus contaminant that could be present in the Factor VIII concentrate manufacturing process stream would be delipidated and presumably more similar to TFF-Supe HEV (prepared according to the method of Example 2) than TFF-HEV (prepared according to the method of Example 1). Thus, the LRV for TFF-Supe HEV is most likely a more accurate assessment of the HEV reduction capacity of the FD/DH treatment step.

Example 6. Preparation of Detergent-Treated TFF HEV Spikes

Figure 3:
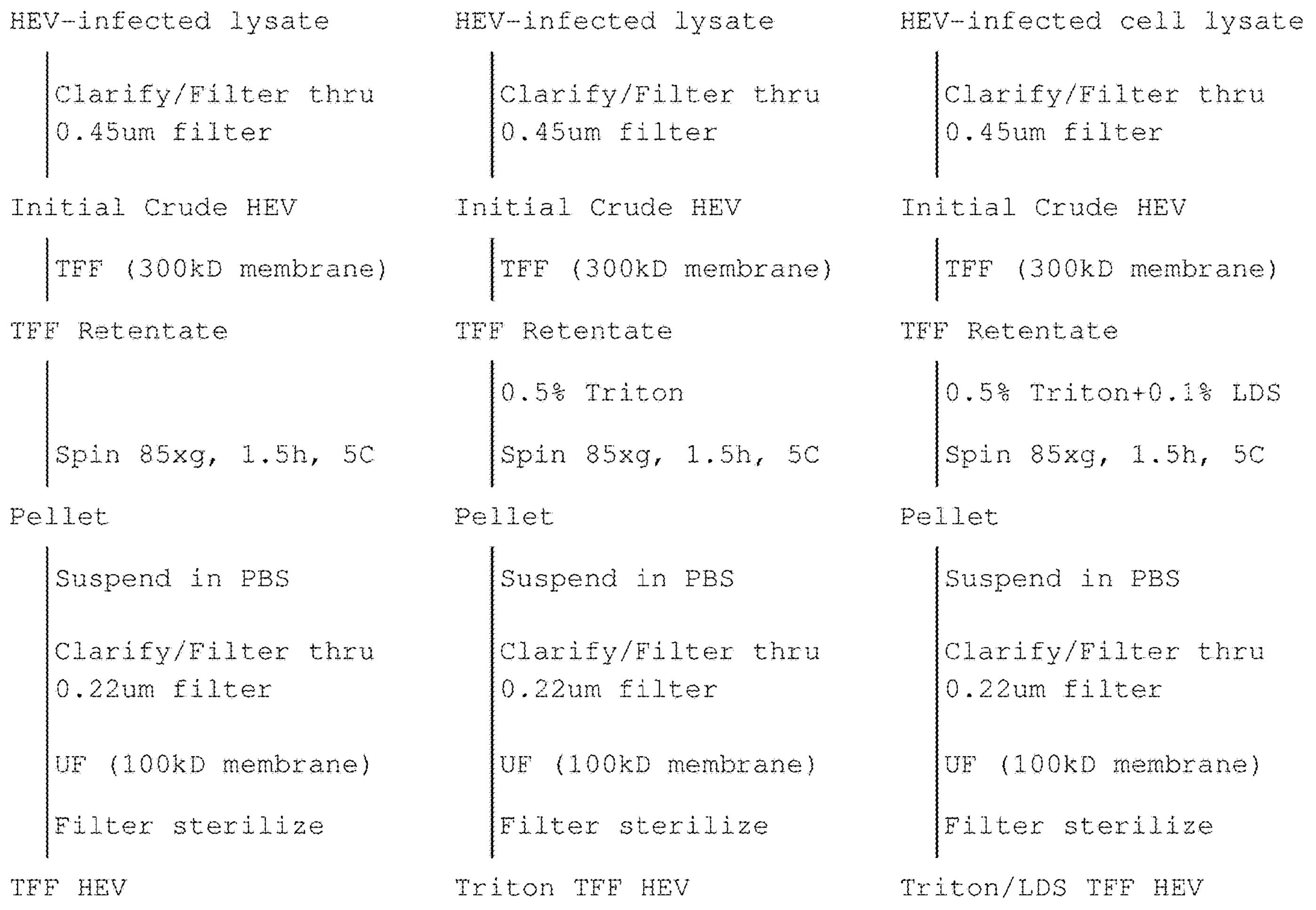
FIG. 3 shows preparation of TFF HEV, Triton TFF HEV and Triton/LDS TFF HEV virus spikes according to some embodiments disclosed herein.

The process for preparing TFF-Supe HEV is relatively time consuming. Therefore, additional methods for detergent treatment were developed for TFF HEV spike preparation. As shown in FIG. 3, the same process for preparing TFF-HEV was followed as in Example 1, except according to some embodiments of the present invention, steps to treat TFF Retentate with various detergents were inserted prior to ultracentrifugation at 85,000×g, 1.5 hours, 5° C. Triton TFF-HEV preparations were incubated with 0.5% Triton X-100 for 1.5 hr, 37° C., while 0.5% Triton X-100+0.1% LDS was used to treat Triton/LDS TFF-HEV spikes. After ultracentrifugation, only the pellets were further processed into virus spikes. The methods to prepare TFF-HEV and detergent-treated TFF-HEV were compared by removing intermediate fractions from the purification processes and titrating for virus as previously described in Example 3. The results are shown in Table 3.

TABLE 3

Comparison of methods to prepare TFF-HEV and detergent-treated TFF HEV

| | $Log_{10}$ Total HEV | | | |
|---|---|---|---|---|
| Virus Spike | Initial | TFF Retentate | Ultracentrifuge Supernatant | Final TFF-HEV Prep |
| TFF-HEV | 8.6 | 8.9 | 8.6 | 8.3 |
| Triton TFF-HEV | 8.6 | 8.9 | 9.1 | 6.8 |
| Triton/LDS TFF-HEV | 8.6 | 8.9 | 8.1 | 8.3 |

Virus recoveries were comparable for the TFF-HEV and Triton/LDS TFF-HEV processes, with the final spike preparations containing approximately 8.3 $log_{10}$ HEV. The Triton TFF-HEV process was less efficient at pelleting virus, as most of the input virus was lost in the Ultracentrifuge Supernatant fraction, and yielded a spike with less than 7 $log_{10}$ HEV.

Example 7. Application of HEV Preparation Methods and Assay in Liquid Heating Experiments Pasteurization is the last step in the albumin manufacturing process and involves heating vials of highly purified product at 60° C. for no less than 10 hours. Virus was prepared as described in Example 6 and spiked into 25% albumin before incubation at 5° C. or 60° C. for 7 hours. Samples were then removed for virus titration and the results are shown in Table 4. As a comparator, data from pasteurization (10 hour, 60° C.) of 25% albumin spiked with TFF-Supe HEV (prepared according to the method of Example 2) are also presented.

TABLE 4

Results obtained from experiments to compare TFF-HEV and detergent-treated TFF-HEV reduction by liquid heating.

| | | $Log_{10}$ HEV Titer | | | | |
|---|---|---|---|---|---|---|
| | Exp | 7 hours | | 10 hours | | |
| Virus Spike | Number | 5° C. | 60° C. | 5° C. | 60° C. | LRV |
| TFF-HEV | VM1910 | 5.6 | 3.3 | ND | ND | 2.3 |
| Triton TFF-HEV | VM1910 | 4.8 | 1.6 | ND | ND | 3.2 |
| Triton/LDS TFF-HEV | VM1910 | 6.1 | 2.3 | ND | ND | 3.8 |
| TFF-Supe HEV | VM1893 | ND | ND | 5.6 | 1.4 | 4.2 |

TFF-HEV was the most heat resistant test virus and showed only a 2.3 $log_{10}$ reduction in titer after heat treatment. The LRV for Triton TFF-HEV was approximately one $log_{10}$ higher, even though its starting titer was approximately one $log_{10}$ lower than TFF-HEV. The LRV for TFF-HEV treated with Triton/LDS was the highest among the three TFF-HEV preparations and slightly lower than the reduction achieved after pasteurization of albumin spiked with TFF Supe HEV, a virus preparation also treated with Triton/LDS.

Example 8. Concentration and Purification of Virus by TFF, Ultracentrifugation, and Ultrafiltration For clarification of virus, frozen crude virus stock was thawed. When preparing a concentrated and purified non-enveloped virus stock 0.5% Triton X-100 and 0.1% LDS were added to the thawed crude virus stock and incubated at 37° C. for 1 hour. Clarification was performed by centrifugation at a speed of 3000 to 8000×g for 15 to 30 minutes at 2° C. to 8° C. The supernatant was removed and retained and the pellet discarded. The supernatant was filtered through a 0.45 μm filter.

For TFF, the TFF system was cleaned and prepared for filtration. The filtered virus stock was clarified.

For ultracentrifugation, the TFF retentate was placed in ultracentrifuge tubes. The tubes are balanced until weights are within ±0.05 g of each other. The tubes are loaded into a swinging bucket rotor and centrifuged at 2° C. to 8° C. for 1.5 hours at approximately 85000×g. At the end of the ultracentrifugation run, supernatant from each of the centrifuge tubes was carefully decanted and discard as liquid waste. The tubes were inverted and allowed to drain on an absorbent towel for approximately 5 minutes at room temperature. After draining, the towel was decontaminated and disposed of.

For ultrafiltration, the ultracentrifugation pellet was resuspended in no less than 5 mL PBS. The pellet suspension was clarified at 3000 to 4200×g for 15 minutes at 2° C. to 8° C. The supernatant was removed and placed into an Amicon® UF filter device to concentrate. If required, PBS was added to bring the final volume to approximately 15 mL (filter capacity is 15 mL). The capped filter device was placed into the centrifuge rotor and the rotor balanced with a counterweight. Centrifugation was performed at approximately 5000×g at 2° C. to 8° C. until the retained sample (concentrated and purified virus stock) final volume was no more than 1 mL (approximate centrifuge time is 15 to 60 minutes).

Definitions

HepG2: Hepatocellular carcinoma cells obtained from the American Type Culture Collection (ATCC number HB-8065)

DMEM: Dulbecco's Modified Eagle Medium

FBS: Fetal Bovine Serum

Titer: Concentration of a substance (virus) in solution or the strength of such a substance determined by titration SK: Spearman-Karber is a statistical method to calculate virus titers in samples with relatively high concentrations of virus. This method is used when the proportion of positive wells at any dilution is >25% (FIG. 1).

MPN: Most Probable Number is a statistical method to calculate virus titers in samples with relatively low concentrations of virus. MPN is used when the proportion of positives wells at all dilutions is <25%.

Poisson: Poisson is a statistical method to calculate virus titers in samples with extremely low concentrations of virus. This method is used when no positive wells are observed.

ATCC: American Type Culture Collection

HEV TFF Retentate: Is the material remaining after clarified HEV-cell lysate has been concentrated using a 300 kD TFF membrane. HEV TFF Retentate is used to prepare TFF HEV spikes.

HEV TFF Supernatant is the effluent remaining after centrifuging HEV TFF Retentate at approximately 84780×g. HEV TFF Supernatant is used to prepare TFF Supe HEV spikes.

$TCID_{50}$ corresponds to 50% Tissue Culture Infective Dose (Endpoint dilution assay). It is a measurement of infectious virus titer that quantifies the amount of virus required to kill 50% of infected hosts of to produce cytopathic effect in 50% of inoculated tissue culture cells.

$A_{280}$: Absorbance measured at 280 nm which is indicative of protein concentration and/or quantity.

AU: Absorbance Units.

Virus spike: virus sample with known viral content.

REFERENCES

1. Okamoto H (2011) Hepatitis E virus cell culture models. Virus Research 161: 65-77.
2. Shukla P, et al (2011) Cross-species infections of cultured cells by hepatitis E virus and discovery of an infectious virus-host recombinant. PNAS. 108 (6): 2438-2443.
3. Shukla P, et al (2012) Adaptation of a Genotype 3 Hepatitis E Virus to Efficient Growth in Cell Culture Depends on an Inserted Human Gene Segment Acquired by Recombination. J Virol 86 (10): 5697-5707
4. U.S. Provisional Patent Application No. 61/431,377
5. U.S. Provisional Patent Application No. 61/554,323
6. U.S. patent application Ser. No. 13/978,839
7. International PCT Application No. PCT/US2012/020830

What is claimed is:

1. A method of purifying hepatitis E virus (HEV) virus propagated in cell culture, the method comprising treating a sample comprising the HEV with a detergent, and purifying the HEV by both centrifugation or ultra-centrifugation and filtration or ultrafiltration, wherein the detergent is a detergent mixture comprising a combination of Triton X-100 and Lithium Dodecyl Sulfate.

2. The method according to claim 1 wherein the virus is produced in an in vitro cell culture.

3. The method according to claim 2, wherein the in vitro cell culture comprises an established cell line.

4. The method according to claim 3, wherein the established cell line is selected from a group consisting of HepG2 (ATCC number HB-8065) and HepG2/C3A (ATCC number CRL-10741).

5. The method according to claim 1, wherein a concentration of Triton X-100 is 0.5% and a concentration of Lithium Dodecyl Sulfate is 0.1%.

6. The method according to claim 1, wherein the step of treating is carried out for 1 hour.

7. The method according to claim 1, wherein purifying the HEV comprises obtaining a supernatant from the ultracentrifugation of a clarified virus-infected cell lysate suspension.

8. The method according to claim 1, wherein the sample is a retentate derived from transflow filtration of a clarified virus-infected cell lysate suspension.

9. A method of measuring a level of HEV in a sample, the method comprising the steps of:

a) providing the sample to a mixture comprising a cell line and a culture medium;
b) incubating the sample to allow propagation of the HEV, if present in the sample, to obtain an incubated portion;
c) treating the incubated portion with a combination of Triton X-100 and Lithium Dodecyl Sulfate, to obtain a treated portion;
d) collecting a part of the treated portion, to obtain a collected portion; and
e) measuring the level of the HEV in the collected portion.

10. The method according to claim 9, wherein the sample is obtained from a mammal.

11. The method according to claim 10, wherein the sample comprises plasma or blood.

12. The method according to claim 9, wherein the HEV is propagated in an in vitro cell culture comprising an established cell line.

13. The method according to claim 9, wherein the cell line is selected from the group consisting of HepG2 (ATCC number HB-8065) and HepG2/C3A (ATCC number CRL-10741).

14. The method according to claim 9, wherein the sample comprises a first retentate obtained by trans-flow filtering a part of the incubated portion through a membrane.

15. The method according to claim 9, wherein the sample comprises a first supernatant obtained by trans-flow filtering a part of the incubated portion through a membrane to obtain a first retentate and centrifugating the first retentate.

16. The method according to claim 9, wherein the sample is treated with at least one detergent or a mixture of detergents to obtain a first solution.

17. The method according to claim 16, wherein the method further comprises:

a) providing a first pellet obtained by centrifugating the first solution;
b) providing a second solution obtained by resuspending the first pellet in PBS;
c) providing a third solution obtained by clarifying the second solution;
d) providing a first filtrate obtained by filtering the third solution using a membrane; and
e) providing a second retentate obtained by ultrafiltering the first filtrate, wherein the second retentate comprises the treated portion.

18. The method of claim 9, wherein measuring the level of the non-enveloped or pseudo-enveloped virus comprises detecting a biological substance.

19. The method according to claim 18, wherein the biological substance comprises a polynucleotide sequence and/or a polypeptide sequence of a virus.

20. The method according to claim 19, wherein the biological substance is an HEV ribonucleic acid.

21. The method according to claim 20, wherein measuring the biological substance comprises:

a) providing a first reaction mixture comprising the HEV ribonucleic acid obtained by mixing a part of the treated portion with a lysis solution;
b) providing a second reaction mixture obtained by adding a first reagent to the first reaction mixture, wherein the second reaction mixture comprises a deoxyribonucleic acid that is complementary to the HEV ribonucleic acid;
c) adding, to the second reaction mixture, a second reagent that is at least partially complementary to a sequence within the deoxyribonucleic acid;
d) adding, to the second reaction mixture, a third reagent that is at least partially complementary to a sequence within the deoxyribonucleic acid;
e) amplifying the sequence encompassed by the second and the third reagents within the deoxyribonucleic acid; and
f) measuring a concentration of the amplified sequence.

22. The method according to claim 21, wherein the second reagent and the third reagent comprises an oligonucleotide sequence selected from the group consisting of:

a. 5'-CGGCTATCGGCCAGAAGTT-3' (SEQ ID NO: 1);
b. 5'-CCGTGGCTATAACTGTGGTCT-3' (SEQ ID NO: 2) and
c. 5'-FAM-TTTTTACGC-ZEN-AGGCTGCCAAGGCC-3IABkFQ-3' (SEQ ID NO: 3).

* * * * *

```
                         SEQUENCE LISTING

<160> NUMBER OF SEQ ID NOS: 3

<210> SEQ ID NO 1
<211> LENGTH: 19
<212> TYPE: DNA
<213> ORGANISM: Artificial Sequence
<220> FEATURE:
<223> OTHER INFORMATION: Synthetic; HEV derived primer

<400> SEQUENCE: 1

cggctatcgg ccagaagtt                                                19


<210> SEQ ID NO 2
<211> LENGTH: 21
<212> TYPE: DNA
<213> ORGANISM: Artificial Sequence
<220> FEATURE:
<223> OTHER INFORMATION: Synthetic; HEV reverse primer

<400> SEQUENCE: 2

ccgtggctat aactgtggtc t                                             21


<210> SEQ ID NO 3
<211> LENGTH: 23
<212> TYPE: DNA
<213> ORGANISM: Artificial Sequence
<220> FEATURE:
<223> OTHER INFORMATION: Synthetic; HEV Probe
<220> FEATURE:
<221> NAME/KEY: misc_binding
<222> LOCATION: (1)..(1)
<223> OTHER INFORMATION: FAM at the 5' end
<220> FEATURE:
<221> NAME/KEY: misc_binding
<222> LOCATION: (9)..(10)
<223> OTHER INFORMATION: ZEN between nucleotides 9 and 10
<220> FEATURE:
<221> NAME/KEY: misc_binding
<222> LOCATION: (23)..(23)
<223> OTHER INFORMATION: 3IABkFQ at the 3' end

<400> SEQUENCE: 3

tttttacgca ggctgccaag gcc                                           23
```